United States Patent
Kandt

(10) Patent No.: US 9,387,114 B2
(45) Date of Patent: Jul. 12, 2016

(54) SPLINT FOR IMMOBILIZING A JOINT

(75) Inventor: Olaf Kandt, Bönningstedt (DE)

(73) Assignee: BSN MEDICAL GMBH (DE)

( * ) Notice: Subject to any disclaimer, the term of this patent is extended or adjusted under 35 U.S.C. 154(b) by 0 days.

(21) Appl. No.: 13/577,022

(22) PCT Filed: Jan. 21, 2011

(86) PCT No.: PCT/EP2011/000241
§ 371 (c)(1),
(2), (4) Date: Oct. 2, 2012

(87) PCT Pub. No.: WO2011/095282
PCT Pub. Date: Aug. 11, 2011

(65) Prior Publication Data
US 2013/0053738 A1 Feb. 28, 2013

(30) Foreign Application Priority Data

Feb. 4, 2010 (DE) .................. 10 2010 001 583

(51) Int. Cl.
*A61F 13/00* (2006.01)
*A61F 5/37* (2006.01)
(Continued)

(52) U.S. Cl.
CPC .............. *A61F 5/05866* (2013.01); *A61F 5/00* (2013.01); *A61F 5/01* (2013.01); *A61F 5/0106* (2013.01); *A61F 5/0123* (2013.01); *A61F 5/0125* (2013.01); *A61F 5/05825* (2013.01);
(Continued)

(58) Field of Classification Search
CPC ........... A61F 5/00; A61F 5/01; A61F 5/0106; A61F 5/0123; A61F 5/0125; A61F 5/37; A61F 13/00; A61F 13/06; A61F 13/061; A61H 1/00; A61H 1/02; A61H 1/0237; A61H 1/024
USPC ........ 602/5, 6, 21, 23, 26; 128/846, 869, 878, 128/882; 601/33–35
See application file for complete search history.

(56) References Cited

U.S. PATENT DOCUMENTS 5,007,415 A * 4/1991 Marion ........................... 602/26
5,316,546 A * 5/1994 Lindh ................... A61F 5/0106
602/16
(Continued)

FOREIGN PATENT DOCUMENTS

EP 0 359 635 A1 3/1990
EP 2 065 019 A1 6/2009

OTHER PUBLICATIONS

International Search Report from the European Patent Office dated May 17, 2011 for PCT/EP2011/000241.
(Continued)

*Primary Examiner* — Alireza Nia
*Assistant Examiner* — Brandon L Jackson
(74) *Attorney, Agent, or Firm* — Shumaker, Loop & Kendrick, LLP

(57) ABSTRACT

A splint for immobilizing a joint including at least one flat body that has two contact surfaces for limbs adjoining the joint to be immobilized and a supporting member in an outer contour having an angular structure for adjusting and bracing an angle between the contact surfaces for the limbs, wherein at least two surfaces are non-displaceably joined together to create a double-walled structure, and wherein a joint axis of the joint to be immobilized forms an angle of less than 60° with a normal of the non-displaceably joined surfaces.

20 Claims, 11 Drawing Sheets

(51) Int. Cl.
*A61B 19/00* (2006.01)
*A61H 1/00* (2006.01)
*A61H 1/02* (2006.01)
*A61H 5/00* (2006.01)
*A61F 5/00* (2006.01)
*A61F 5/058* (2006.01)
*A61F 13/06* (2006.01)
*A61F 5/01* (2006.01)

(52) U.S. Cl.
CPC ............... *A61F13/00* (2013.01); *A61F 13/06* (2013.01); *A61F 13/061* (2013.01); *A61H 1/00* (2013.01); *A61H 1/02* (2013.01); *A61H 1/024* (2013.01); *A61H 1/0237* (2013.01); *A61F 5/37* (2013.01)

(56) References Cited

U.S. PATENT DOCUMENTS

| | | | |
|---|---|---|---|
| 5,772,620 A | 6/1998 | Szlema et al. | |
| 5,800,371 A * | 9/1998 | Winn | A61F 5/3715 473/207 |
| 6,342,043 B1 * | 1/2002 | Gottsmann et al. | 602/12 |
| 7,182,740 B1 * | 2/2007 | Castillo | 602/5 |
| 8,328,745 B2 * | 12/2012 | Einarsson | A61F 5/0106 602/16 |
| 2006/0079819 A1 * | 4/2006 | Evans et al. | 602/6 |

OTHER PUBLICATIONS

EP 11700896.1 Office Action dated Aug. 18, 2014.

* cited by examiner

Fig. 6
a) 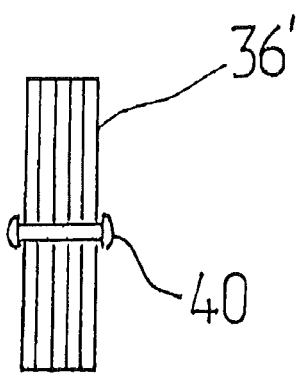
b) 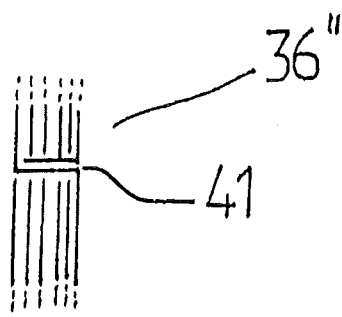
c) 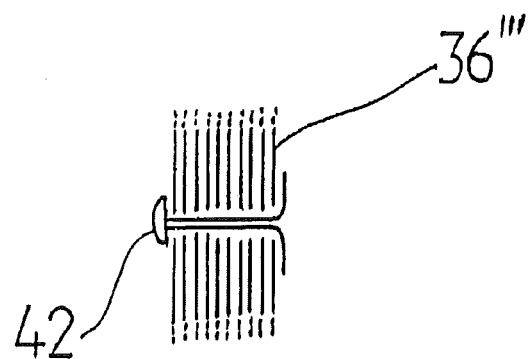

SPLINT FOR IMMOBILIZING A JOINT

CROSS-REFERENCE TO RELATED APPLICATIONS

This application claims priority to PCT/EP2011/000241 filed Jan. 21, 2011, which claims priority to DE 10 2010 001 583.0 filed Feb. 2, 2010, the entirety of both of which are incorporated by reference herein.

TECHNICAL FIELD AND BACKGROUND OF THE INVENTION

The invention concerns a splint for immobilization of a joint, which is to be worn on the joint to be immobilized, wherein the splint comprises at least one flat body that has at least two contact surfaces for limbs adjoining the joint to be immobilized, wherein a supporting member is provided, which in its outer contour has an angle structure for adjusting and bracing an angle between the contact surfaces for the limbs.

When the muscles of the human body are strained, injuries repeatedly occur in daily life, at work, and during recreation, which make it necessary to immobilize them with inclusion of one or more joints, in order to ensure complication-free healing.

Injuries to the bones, tendons, muscles, nerves or blood vessels often involve considerable pain. This is true especially for fractured bones and soft tissue injuries. Symptoms of this are pain upon movement, exertion, pressure or extension, as well as bleeding. Especially common are injuries in recreational sports and athletics, as well as in daily life. Many of the injuries and pain conditions occurring in these areas necessitate the provision of a splint.

For minor injuries and sprains, in addition to immobilization it is also customary to apply cold and elevate the affected body part. Furthermore, immobilizing tape dressings, ointment dressings, and zinc paste dressings, as well as physical therapy, braces and bandages are used.

Splint dressings are used exclusively for serious injuries or pain conditions. The affected body part with the inclusion of one or more joints is immobilized by use of a splint or ready-to-wear brace in this case. Splints made from materials such as natural plaster, thermoplastics, fiberglass or polyester, as well as ready-to-wear braces made of plastic or aluminum are usually employed for this.

Ready-to-wear braces and custom-made splints differ in that the immobilization of one or more joints after applying a custom-made splint requires fixation with a bandage. Ready-to-wear braces, on the other hand, are provided with hook-and-eye closure systems that perform the fixation. Due to the more costly manufacturing, ready-to-wear braces are used exclusively in long-term care situations, for cost factors. For short-term applications, splints are used that are prepared and individually adjusted by the physician himself.

Splint care is time-consuming and cost-intensive, since individual preparation and adjustment is necessary. Due to the heavy weight of the material with sharp edges caused by the processing method, such splints are often uncomfortable to wear. The applying and preparing of such splint dressings, such as the shaping of the plaster into the medically desired splint with no sharp edges, requires special skills and knowledge, which requires special education and training.

With such known splint systems it is not possible to quickly apply a splint at the scene of an injury just suffered, so that the affected joint or body part can be immobilized to prevent further worsening of the injury in the near future. Nor can such splints be used when injuries affecting the skin are to be treated, since traditional splint systems cannot be removed flexibly and then put back in place again.

BRIEF SUMMARY OF THE INVENTION

The problem of the invention is to provide splints for immobilization of a joint, which are to be worn on the joint to be immobilized, with which immediate care can be provided on an injury for the immobilization of a joint, at the same time affording better wearing comfort, being more cheap to produce and package, and having increased stability.

This problem is solved by a splint for immobilization of a joint, which is to be worn on the joint to be immobilized, wherein the splint comprises at least one flat body, the splint having at least two contact surfaces for limbs adjoining the joint to be immobilized, wherein a supporting member is provided, which in particular in an outer contour has an angle structure for adjusting and bracing an angle between the contact surfaces for the limbs, said splint being further modified in that at least two surfaces arranged in the assembled state of the splint on the sides of the contact surfaces facing away from the limbs are provided, being immovably joined together to form a double-wall or multiple-wall structure at least in some sections, while a joint axis of the joint to be immobilized or of an edge between the contact surfaces or an intersection of the extensions of at least two contact surfaces makes an angle of less than 60° with a normal of the immovably joined-together surfaces. Preferably, the supporting member serves to adjust and brace an angle between the contact surfaces for the limbs.

This problem is moreover solved by a splint for immobilization of a joint, which is to be worn on the joint to be immobilized, wherein the splint comprises at least one flat body that has at least two contact surfaces for limbs adjoining the joint to be immobilized, wherein a supporting member is provided, which in an outer contour has an angle structure for adjusting and bracing an angle between the contact surfaces for the limbs, said splint being further modified in that at least two surfaces arranged in the assembled state of the splint on the sides of the contact surfaces facing away from the limbs are provided, being immovably joined together to form a double-wall or multiple-wall structure at least in some sections, while a joint axis of the joint to be immobilized makes an angle of less than 60° with a normal of the immovably joined-together surfaces.

The immovable joining of several surfaces that protrude from the bottom of the contact surfaces has the effect, according to the invention, that the surfaces not only stabilize the contact surface more, but also stabilize each other. This means that the supporting member is protected, for example, against sideways folding away, which benefits the stability of the splint. By immovably joined is meant, according to the invention, that a displacement of the surfaces relative to one another is prevented both in the lengthwise direction of the splint and also perpendicular to the contact surfaces. A surface in the context of the invention is in particular a flat body that has an in particular predeterminable thickness.

In the context of the present invention, a "double-wall" or "multiple-wall" structure means that two or more surfaces are arranged parallel to one another with little or no spacing. This is illustrated by a case in which the supporting member is folded together from a flat body, resulting after the folding in an essentially rectangular cross section. The rectangular cross section of such a supporting member has two outer walls, only one of which, however, forms a double-wall or multiple-wall structure at least in some sections, according to the invention.

This double-wall or multiple-wall design of the side walls, i.e., the walls projecting downward from the receiving surfaces, means that such an essentially rectangular cross section cannot be transformed by a sideways force into a diamond-shaped cross section which would have a lesser supporting action.

The normal to a surface is a line which is perpendicular to the surface. The feature that a joint axis of the joint to be immobilized makes an angle of less than 60° with a normal of the immovably joined-together surfaces thus means in the context of the invention that the joint axis passes through the surfaces perpendicularly or at an angle of up to 60°, but does not lie in the surfaces. In this way, for the stabilization of the joint to be immobilized, the fact that the surfaces, especially in the assembled state, have good rigidity to shearing forces, i.e., against bending in the surface, even if they are not very rigid to bending which is directed perpendicular to the surface, is utilized. Preferably, the joint axis of the joint to be immobilized or an edge between the contact surfaces and the normal of the immovably joined-together surfaces make an angle of less than 45°, more preferably an angle of less than 30°, especially preferably an angle of less than 15°. Preferably, the normals of the immovably joined-together surfaces and the joint axis or the edge or the intersection are essentially parallel to each other.

It is preferable that two pairs of at least two surfaces are provided which are arranged in the assembled state of the splint on the side of the contact surfaces facing away from the limbs, said surfaces being immovably joined together to form a double-wall or multiple-wall structure at least in some sections and arranged symmetrically with respect to one another about a lengthwise axis of the splint. This yields a symmetrical triangular or trapezium shape, producing an especially good stability of the splint.

Supporting members of the invention can bridge a concave or a convex side of a splint or be arranged to the side of it.

In one preferred embodiment, the supporting member has a sheetlike material and is folded or can be folded into a three-dimensional form having an outer contour with an angle structure for configuring the contact surfaces of the flat body. Such a folded or foldable structure has a shape in cross section that provides a supporting action, with surfaces protruding from the bottom of the contact surfaces, i.e., side surfaces which according to the invention form a double-wall or multiple-wall structure at least in some sections. The basic shapes that are especially suitable for this are an equilateral triangle, a symmetrical trapezium, or a rectangular shape.

If at least one strap is arranged preferably in the flat body in the region of the contact surface for a forearm, which strap can be folded out and in the assembled state of the splint can be introduced or is introduced into at least one slit in the sheetlike material of the supporting member, a secure and immovable contact surface with the supporting member is achieved, along with a double-wall design of the surfaces projecting from the bottom of the contact surfaces in some sections. The strap surface leading downward from the contact surface to the slit in the surface of the supporting member is arranged parallel to one side surface and, as a result of the connection to the supporting member, immovably on the supporting member or the corresponding surface of the supporting member. This is an especially simple and stable design for a connection. Several straps can also be provided, said straps being able to engage on both sides of the supporting member.

In an alternative or additional embodiment, which is likewise preferred, the supporting member comprises several flat bodies arranged parallel to each other, and joined to each other. In this embodiment, a common supporting member is formed from several flat bodies, the flat bodies being oriented parallel to each other, for example, stacked on one another. The orienting of the flat bodies as a supporting member is such that the surfaces of which the supporting member is composed project downward from the contact surfaces for the forearm and for the palm of a hand.

In this embodiment of the invention, a quasi-solid supporting member is produced from several flat bodies, which is quick and easy to do with suitable prefabricated shapes. Preferably, the supporting member is or can be connected at an outer contour with an angle structure to a side or bottom of the flat body facing away from the limbs. In the context of the invention, the bottom of a flat body is defined as being the side of the flat body facing away from the limbs and from the joint to be immobilized. Preferably, also, several supporting members will be used, especially ones that are parallel to each other. These can be arranged at the side of the joint to be immobilized.

The connection of the flat bodies to each other and/or the connection of the supporting member to the flat body preferably comprises an adhesive, a rivet, a screw, a clamp, a strap or a hook-and-eye connection. By a strap connection is meant in this context for example the case where a bendable sheet element or insert element of a sheetlike strap of a flat body is pushed through a corresponding slit of another flat body and in this way fixing is accomplished, which can be loosened if necessary. By an adhesive connection in the context of the invention is also meant a glue connection.

The supporting member constructed from flat bodies that are joined together is preferably punched out, in particular at first the flat bodies are stacked and joined together and then the entire supporting member is punched out. Prepunched flat bodies can also be joined to form a supporting member according to the invention. Supporting members assembled in this manner, especially glued, produce lightweight and highly stable splints.

Preferably, supporting members with different angles for the joint to be immobilized are produced and/or kept in stock, so that the correct angle position for a joint can be used during their application.

A supporting member constructed from two or more layers can be applied to the splint as a block or divided, for example, with two smaller angles. This allows easier stacking during storage.

In a further modification of the invention, it is preferable that the supporting member in the folded state encloses a cavity extending along the splint, in which cavity a second supporting member is arranged or into which cavity a second supporting member can be introduced. The first supporting member, which is folded, and/or the second supporting member which can be introduced into the cavity or is arranged in it, have according to the invention a double-wall or multiple-wall structure, as already described above. Such a dual support structure with a foldable first supporting member and a quasi-solid or solid second supporting member ensures yet further increased stability of the support structure.

Preferably, the flat body or bodies consist of a high tensile strength material, especially cardboard or corrugated cardboard. These materials have tensile strength in their two-dimensional plane, but can be easily bent about fold lines. Other materials, such as plastics, which are more elastic in a direction perpendicular to their surface, can be bent even without fold lines. If the flat body or supporting member is made of corrugated cardboard, the interior ribs of the corrugated cardboard are preferably at least partly orthogonal to the bending of the flat body or supporting member or oriented at least partly parallel to the fold lines of the flat body and/or supporting member. Thus, the ribs are oriented at least partly along the spine of a bend of the flat body and support the stabilizing action of the bend. Corrugated cardboard is especially stable against bending in the direction of the ribs.

In a supporting member constructed from several interconnected layers of corrugated cardboard, the corrugations of the different layers of the corrugated cardboard are preferably oriented in parallel. To increase the tensile strength in different directions, it is furthermore advantageously provided for the corrugations of the different layers of the corrugated cardboard to be oriented in different directions, especially perpendicular to each other, especially in an alternating sequence of layers.

Preferably, the flat body and the supporting member consist of a single-piece flat body. In this way, all parts which can be assembled into a splint are available within easy reach.

The splints of the invention can be fastened to the joints to be immobilized or the adjacent body parts, for example, by wrapping with bandaging material or by lashing with belts or similar fixation means.

Splints according to the invention can be used on various joints, including the wrist, the elbow, the ankle or the knee. Small versions of splints are also possible and can be used on finger joints or toe joints.

Supporting members can be arranged according to the invention in the crook of a joint, i.e., the hollow of the knee, for example, on its outside, i.e., along a knee cap, or laterally outside, such as on either side of an elbow joint. Each of these versions affords advantages. Thus, supporting members arranged on either side of an elbow joint can protect the elbow head from shocks and breaks. A supporting member arranged on a knee cap exerts its supporting action close to the bone, while a supporting member arranged at the hollow of the knee engages with a smoother surface.

It may also happen that, as a result of further superficial injuries, a region of the joint or of the adjacent limbs is not available for support purposes. Thus, it is possible to adapt the arrangement and selection of the splint and of the supporting member to specific injury types and situations.

The problem is moreover solved by a splint for immobilization of a joint, which is to be worn on the joint to be immobilized, wherein the splint comprises at least one flat body, the splint having at least two contact surfaces for the limbs adjacent to the joint to be immobilized, wherein a supporting member is provided and is fashioned as a shaped body, whose angle between at least two surfaces of the shaped body that are connected to the sides facing away of the contact surfaces of the flat body dictate the angle between the contact surfaces.

Preferably, the shaped body is fashioned as a single piece. However, it can also be of two-piece or multiple-piece design. In the case when the shaped body is of two-piece or multiple-piece design, the individual pieces are preferably connectable, so that together they form a shaped body. Preferably, the shaped body has at least three surfaces, which are oriented toward the flat body and dictate at least two angles of the flat body. In this case, structures which are more complex in terms of their shape can also be provided. Preferably, the supporting member has in one outer contour an angle structure for adjusting and bracing an angle between the contact surfaces for the limbs.

Preferably, the shaped body is embodied in solid fashion, which enables quick and cheap fabrication. Preferably, the shaped body is fashioned from a single material. Preferably, the density of the shaped body lies in a range of 0.01 g/cm³ to 3 g/cm³, especially up to 0.5 g/cm³. Accordingly, the shaped body is also preferably connected to the flat body or the flat bodies by an adhesive, riveting, screwing, clamping, strapping, or one or more hook-and-eye connections. By solid is also meant especially in the sense of the invention that several layers of cardboard or corrugated cardboard are joined together.

The shaped body can consist, for example, of balsa wood or a foam plastic, preferably a closed-pore foam plastic. Especially suitable for this are hard foams such as polyurethane hard foam, polyethylene hard foam, polycarbodiimide hard foam or similar materials. It is preferable for the compressive strength to be between 0.3 and 15 MPa. The compressive strength and/or the tensile strength of the shaped body or the supporting member should be such that a sufficient stability of the splint for the particular joint is made possible, such as the knee joint, the ankle, the elbow joint or the wrist. Thus, for example, there should be a lower compressive strength and tensile strength for the wrist and the elbow joint than for the ankle or the knee joint, since the load there will be less. It is possible for the skilled person to determine the compressive strength or the tensile strength by means of the particular loads occurring at the particular joint.

The shaped body, furthermore, can consist of a composite material, such as a composite material of a foam plastic with a metal, which can enclose the foam plastic at least in part. Suitable as the metal is aluminum or titanium, for example. The composite material is present preferably in a sandwich structure. The shaped body preferably also has two outer surfaces, whose normals make an angle of 60° with an axis of the joint or an edge between the contact surfaces of the flat body.

The invention will be described hereafter, without limiting the general notion of the invention, by means of exemplary embodiments making reference to the drawings; reference should be made to the drawings in respect of any features of the invention not explained more closely in the text.

BRIEF DESCRIPTION OF THE DRAWINGS

In the drawings:

FIG. 6 shows schematic cross-sectional representations through other flat bodies according to the invention.

DETAILED DESCRIPTION OF THE INVENTION

In the following figures, the same or similar elements or corresponding parts are given the same reference numbers, so that they do not have to be introduced anew.

Figure 1:
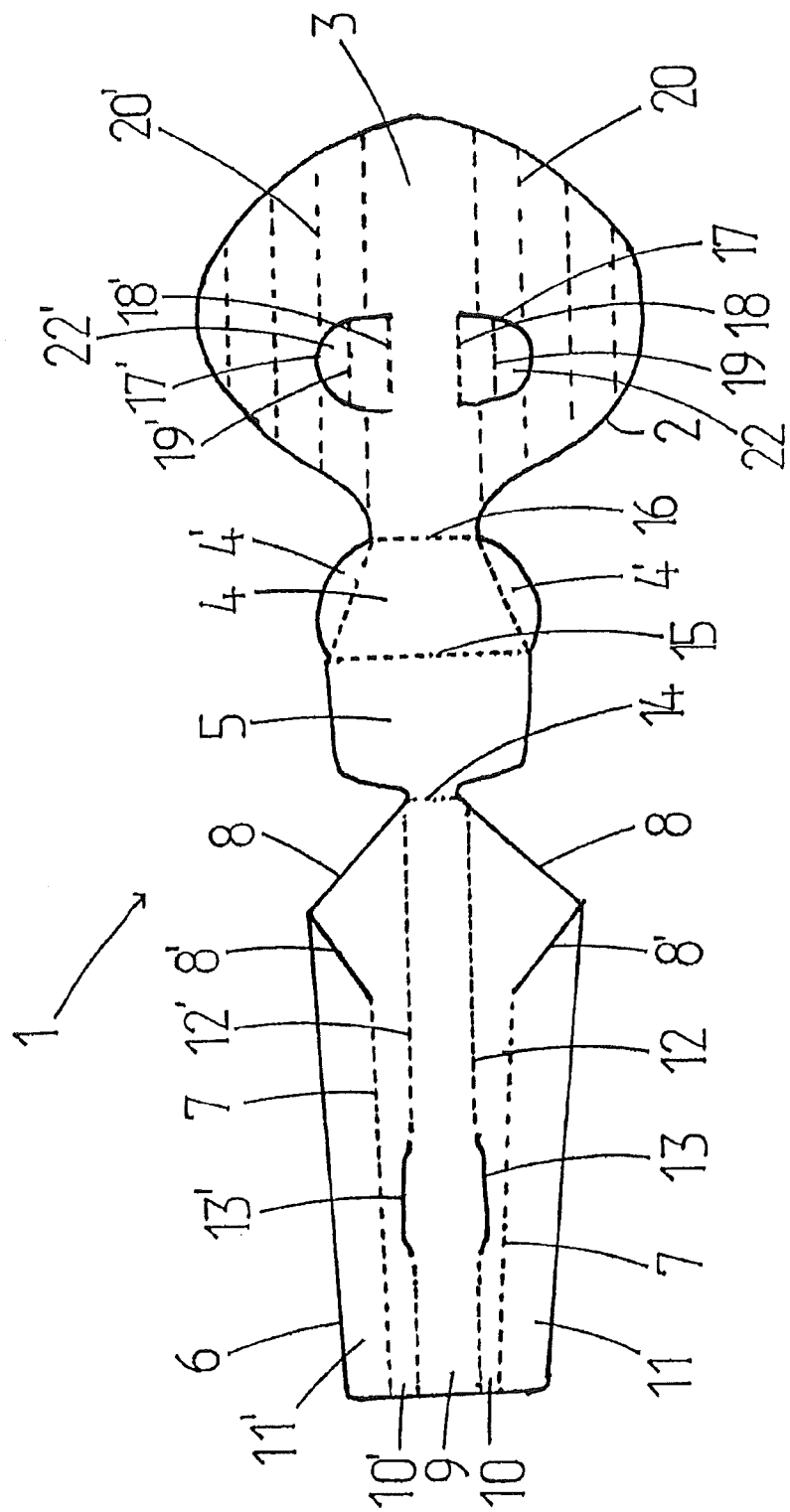
FIG. 1 shows a schematic representation of a splint according to the invention in a two-dimensional view.

FIG. 1 shows a splint according to the invention in terms of a splint 1 for immobilization of a wrist, in a schematic two-dimensional representation, that is, in the unfolded state. The flat body 2 can be folded about the fold lines (shown in dashed fashion) to produce a splint for a wrist. The fold lines can be punched out or perforated. Solid lines in the flat body 2 represent slits, i.e., the adjacent flat elements or surfaces of the flat body 2 are not joined together at these sites. The slits can be directly punched out or initially perforated so as to be opened only when the splint is assembled.

The flat body 2 comprises a contact surface 3 for a forearm, which widens perpendicular to the longitudinal axis of the flat body 2. This produces wings which can be folded upward about fold lines 20, 20' in order to enclose a forearm. Next to the contact surface 3 for a forearm there is a contact surface 4 for the palm of a hand, which has sideways bendable contact surfaces 4' for a thumb. This is a splint that can be used on both the right forearm and the left forearm; on either side of the contact surface 4 for the palm of a hand there are contact surfaces 4' for a thumb. Next to the contact surface 4 for the palm of a hand there is a contact surface 5 for fingers.

The contact surfaces 3, 4 and 5 constitute the part of the splint 1 that is placed directly on the wrist to be immobilized and the adjacent body parts. The contact surfaces 3, 4 and 5 can each be folded about transverse folds 15 and 16 relative to each other. Thus, the angle structure can be adjusted so that a hand with its palm can be bent upward relative to the forearm.

This structure is adjoined on the other side of another transverse fold 14 by a flat structure for a supporting member 6. The supporting member 6 consists of a sheetlike part of the flat body 2, having a fold line structure which can be folded into an essentially rectangular body. A bottom 9 runs centrally, adjoined by side surfaces 10 and 10' on both sides, which are in turn adjoined by two parts at the top side 11, 11'. The fold lines which separate the side surfaces 10, 10' from the top sides 11, 11' form, together with an angle structure 8, 8', an outer contour 7, on which the contact surfaces 3, 4, 5 for a forearm, a palm and fingers are placed.

The fold line for the bottom of the supporting member 6 is denoted by the reference numbers 12, 12'. These fold lines 12, 12' each have a slit 13, 13', into which a strap can be inserted by a strap insert piece 22, 22'.

The corresponding straps 17, 17' are provided in the contact surface 3 for a forearm of the flat body 2. They are arranged in mirror symmetry. The straps 17, 17' have a strap fold line 18, 18' in the contact surface 3 and a strap fold line 19, 19' in the strap, adjoined by strap insert pieces 22, 22'.

To assemble or put together the splint 1, one proceeds as follows. First, the supporting member 6 is folded by first folding the side surfaces 10, 10', 11, 11' downward about the fold lines 12, 12', so that they project essentially perpendicularly downward. Next, the surfaces 11, 11' of the tops are bent inward once again by 90°, so that they overlap. The side surfaces 10, 10' with the angle structures 8, 8' then remain at the side.

The supporting member folded in this way is rotated about the transverse fold 14 and brought under the contact surfaces 3, 4, 5. In the process, the contact surface 5 for the fingers comes to lie on the angle structure 8, the contact surface 4 for a palm on the angle structure 8' and the contact surface 3 for a forearm on the fold line which is denoted by the reference number 7 for the outer contour. In the exemplary embodiment shown, the contact surface 4 for a palm is bent by around 30° from the contact surface 3 for a forearm.

To secure the supporting member 6 to the contact surfaces 3, 4, 5, the straps 17, 17' are forced downward, so that the surfaces between the fold lines 18 and 19 or 18' and 19' are parallel to the side surfaces 10, 10' of the supporting member 6. The surfaces of the straps 17, 17' beneath the fold lines 19, 19' are strap insert pieces 22, 22' and serve as flaps of the straps 17, 17' that are pushed through the slits 13, 13' in the flat body 2 of the supporting member 6. In this way, the contact surface 3 for a palm is secured to the outer contour 7 of the supporting member 6. The contact surfaces 4 and 5 follow the angle structure 8, 8'.

Figure 2:
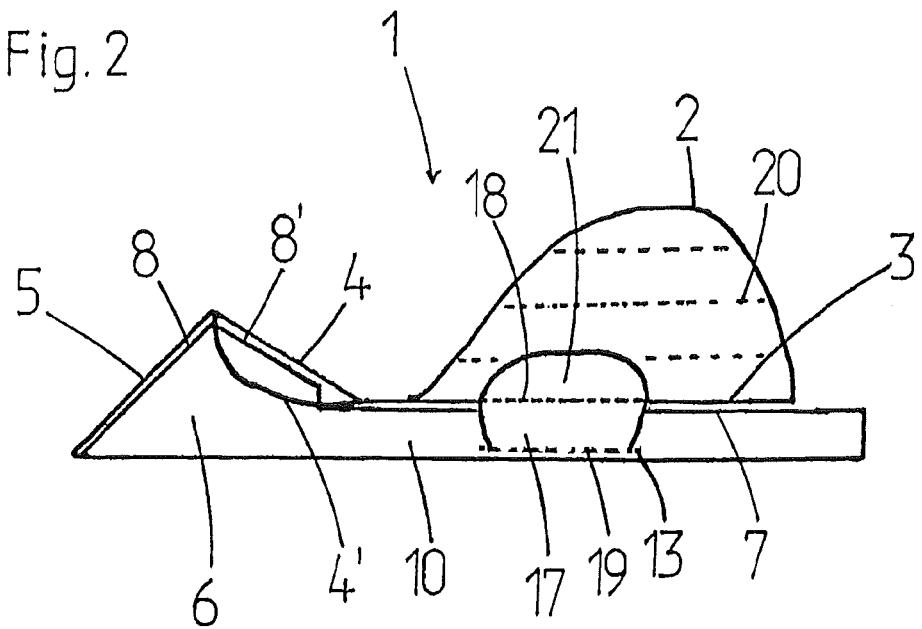
FIG. 2 shows a schematic side view of the splint of FIG. 1 in the assembled state.

FIG. 2 shows schematically the outcome of the above-described folding and strapping process in a side view. On the top, at the left and right in FIG. 2, there is a contact surface 5 for fingers and a contact surface 4 for a palm. The latter is shown by a broken line, since the side view impinges on the fold line that separates the contact surface 4' for the thumb from the contact surface 4 for a palm. Next comes the contact surface 3 for a forearm, the surfaces on either side of the contact surface 3 being bent upward about the fold lines 20 in the representation of FIG. 2.

Beneath the contact surfaces 3, 4, 5 is shown the supporting member 6, looking at the side surface 10. The outer contour 7, produced by the side surface 10, consists of the contour in the region of the contact surface 3 and the angle structure 8, 8' in the region of the contact surfaces 5 and 4. For better visibility, a gap has been left between the respective lines of the drawing that is not present or only minimally present in reality, and only occurs in some places.

In the laterally raised areas of the contact surface 3 for a forearm one can see a recess 21, in which the strap 17 was present in the flat state. This has now been bent downward and inserted by its insert piece into the slit 13. The side view in FIG. 2 is therefore oriented in this place to the strap fold line 18 in the contact surface 3, and therefore this is shown by a broken line. The same applies for the strap fold line 19 in the strap.

The joint axis of a wrist runs in the plane of the image in the representation of FIG. 2.

Figure 3:
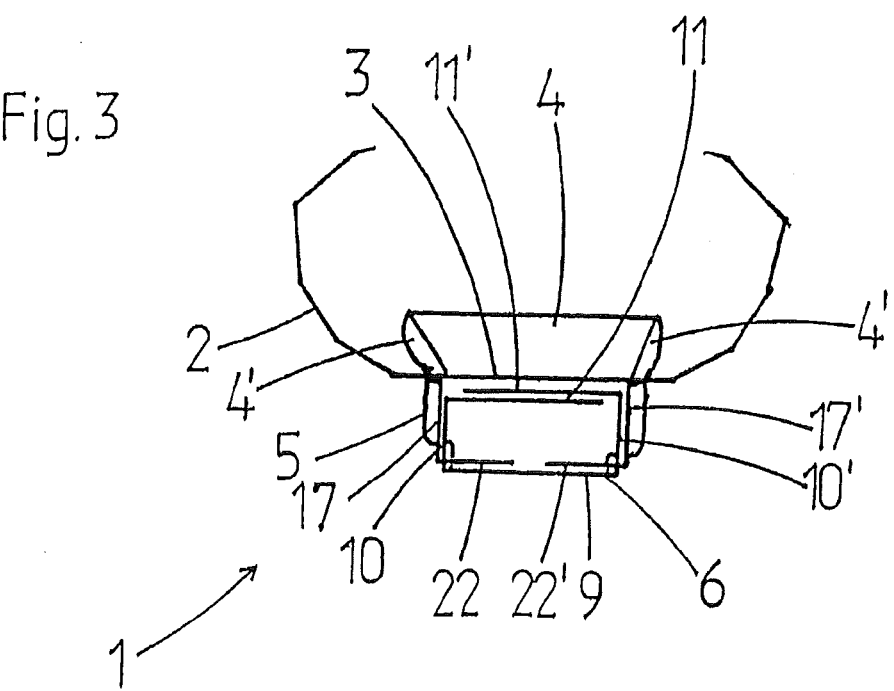
FIG. 3 shows a schematic rear view of the splint of FIG. 1 in the assembled state.

FIG. 3 shows a schematic rear view of the splint 1 of FIG. 2. One can see the symmetrical arrangement, where the flat body 2 in the upper region has the upwardly bent sides of the contact surface 3 for a forearm. This is followed by the contact surface 4 for a palm with the contact surfaces 4', arranged at the sides, for the thumb, on the left or right.

The double-wall or multiple-wall structure according to the invention of the surfaces beneath the contact surfaces is clearly shown in FIG. 3. The supporting member 6 in the folded state has a rectangular cross section. This has the bottom 9 and side surfaces 10, 10'. One can see that the tops 11, 11' are folded inward and overlap each other. These are located underneath the contact surface 3 for a forearm.

From the contact surface 3 for a forearm, the straps 17, 17' are bent downward and are partly parallel to the side surfaces 10, 10'. The straps 17, 17' are each folded inward about a fold, so that the outermost surface pieces, the strap insert pieces 22, 22', are inserted through slits in the side walls 10, 10' into the rectangular cross section and lie against the bottom 9 of the supporting member 6. They are secured in this way.

The slits 13, 13' and the fold lines 18, 18', 19, 19' are not shown separately in FIG. 3, but they correspond to the fold lines of FIG. 1 and FIG. 2.

Since the strap insert pieces 22, 22', which are also shown in FIG. 1, lie against the bottom 9 of the supporting member 6, it is not possible for the contact surface 3 to be pulled upward relative to the supporting member 6. This would result in a downward bending of the strap insert pieces 22, 22', but that is prevented by the bottom 9 of the supporting member 6. Thus, the straps 17, 17' are secured immovably relative to the supporting member 6 by its side surfaces 10, 10'. In the lengthwise direction of the splint 1, an immovable fixation is accomplished by adapting the length of the slits 13, 13' and the width of the straps 17, 17' at the location of the fold lines 19, 19'.

FIG. 3 furthermore shows that the contact surface 4 for a palm is also adjoined by the contact surface 5 for fingers. This is for the most part hidden by the supporting member 6. However, since it is broader than the supporting member 6, it protrudes slightly to the side beyond the supporting member 6. The contact surface 5 is at the front end of the splint, as can also be seen in FIG. 2, and as can also be seen from FIG. 1 it is connected to the bottom 9 of the supporting member at the transverse fold line 14. For this, the contact surface 5 tapers somewhat toward the tip.

The axis of a wrist runs in the horizontal plane of the drawing in the representation of FIG. 3. A normal to the side walls 10, 10', which are joined to the straps 17, 17' in double-wall fashion, runs parallel to the axis of the joint, i.e., at an angle of 0°. If, instead of the rectangular cross section shown, a symmetrical triangular or trapezium cross section were used, this angle would be greater than 0°.

Figure 4:
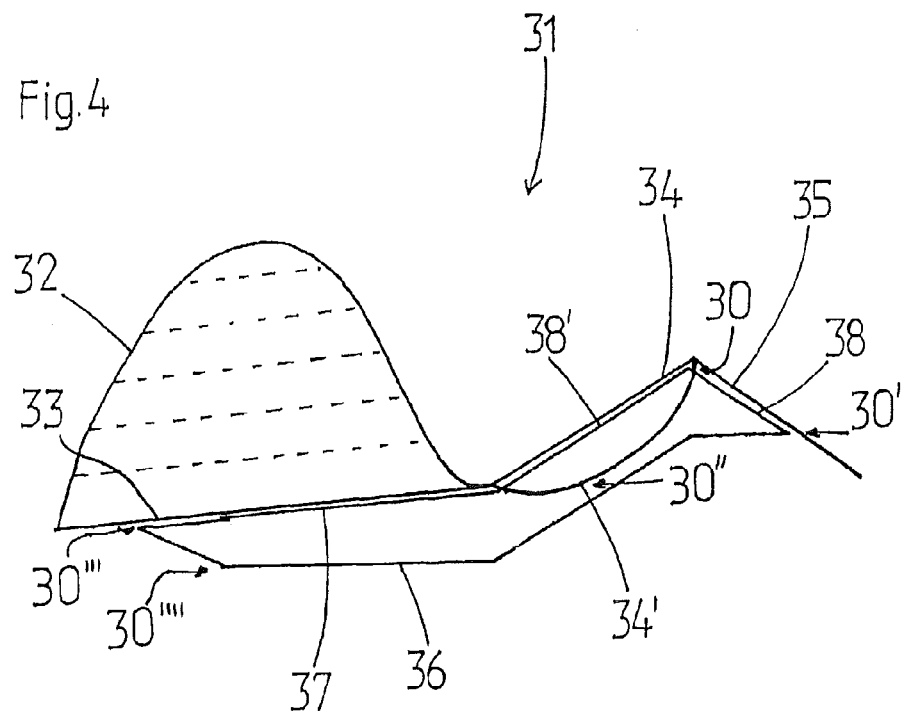
FIG. 4 shows a schematic side view of another splint according to the invention.

FIG. 4 shows schematically an alternative exemplary embodiment of a splint 31 according to the invention in a side view. The contact surfaces 33 for a forearm, 34 for a palm, 34' for a thumb and 35 for fingers correspond to those from the exemplary embodiment of FIG. 1. It is likewise shown how the contact surface 33 can then be bent to the side so that a forearm can be enclosed.

Unlike in the exemplary embodiments of FIG. 1 to 3, in the exemplary embodiment of FIG. 4 a separate supporting member 36 is provided, which is arranged underneath the contact surfaces 33, 34, 35 and joined to the latter. The separate supporting member 36 has an outer contour with an angle structure 38, 38' that serves to shape and maintain the contact surfaces 33, 34 and 35. Corresponding edges 30 to 30'''' or edge layers are formed in this way.

Figure 5:
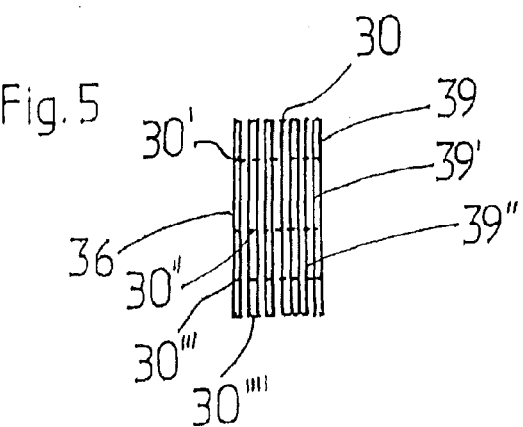
FIG. 5 shows a schematic cross-sectional representation through a flat body according to the invention.

FIG. 5 shows schematically in cross section that a corresponding supporting member 36 is constructed from a plurality of flat bodies 39, 39', 39'', and so on, stacked on one another. The transversely running broken lines correspond to the corner points or edges 30 to 30'''' of the structure that is shown schematically from the side in FIG. 4. Each individual vertical line in FIG. 5 constitutes a schematic representation of a flat body. The flat bodies 39, 39', 39'', and so on, are adhesively bonded to each other in the exemplary embodiment of FIG. 5. In this case, a normal to the flat bodies 39, 39', 39'', which runs in the horizontal plane of the drawing, makes an angle of 0° with the axis of the wrist.

FIGS. 6a) to 6c) show three different examples of how corresponding flat bodies can be joined together in a supporting member. FIG. 6a) shows a supporting member 36' with several flat bodies, joined by a rivet 40. Several rivets 40 can also be used, each one having two heads.

In FIG. 6b), a supporting member 36'' has a strapping 41. This means that two outwardly situated flat bodies each have a strap, which is led through a slit in the inner flat bodies and then bent or folded at the other side and led out once again. This can be done crosswise from both sides or in another suitable arrangement.

FIG. 6c) shows by means of another supporting member 36''' with a plurality of flat bodies an especially simple connection using round head clamps 42 with two feet, each of the flat bodies in the supporting member 36''' having a hole for a round head clamp on the same side, the clamp being inserted through the corresponding hole. At the opposite side, the feet of the round head clamps are bent apart, so that a simple and secure purchase can be produced.

The splints and supporting members shown in FIG. 4 to 6 constitute examples of very stable splints and supporting members that can be easily made from flat bodies. These, like the exemplary embodiment of FIG. 1 to 3, can be fabricated and packaged easily and quickly.

Figure 7:
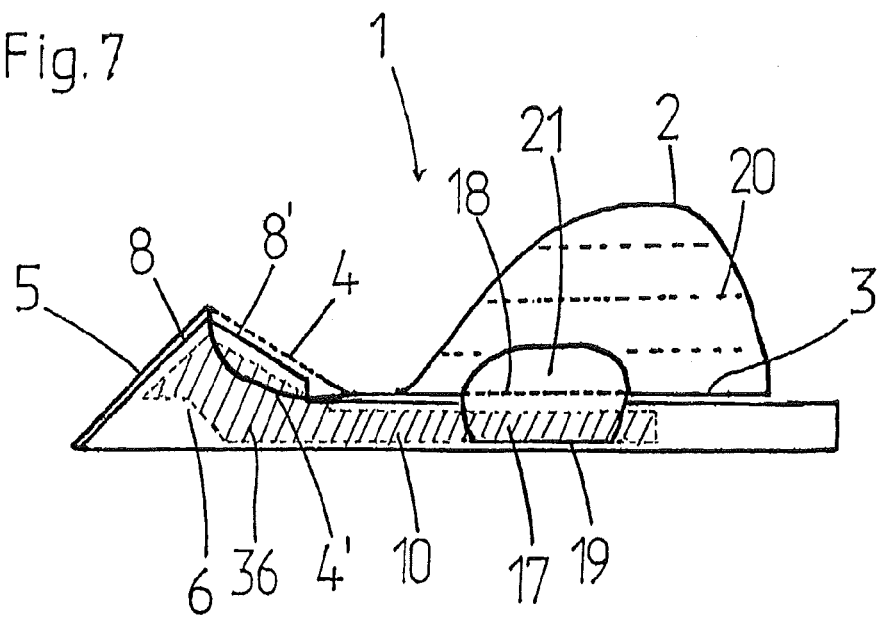
FIG. 7 shows a schematic side view of another splint according to the invention.
Figure 8:
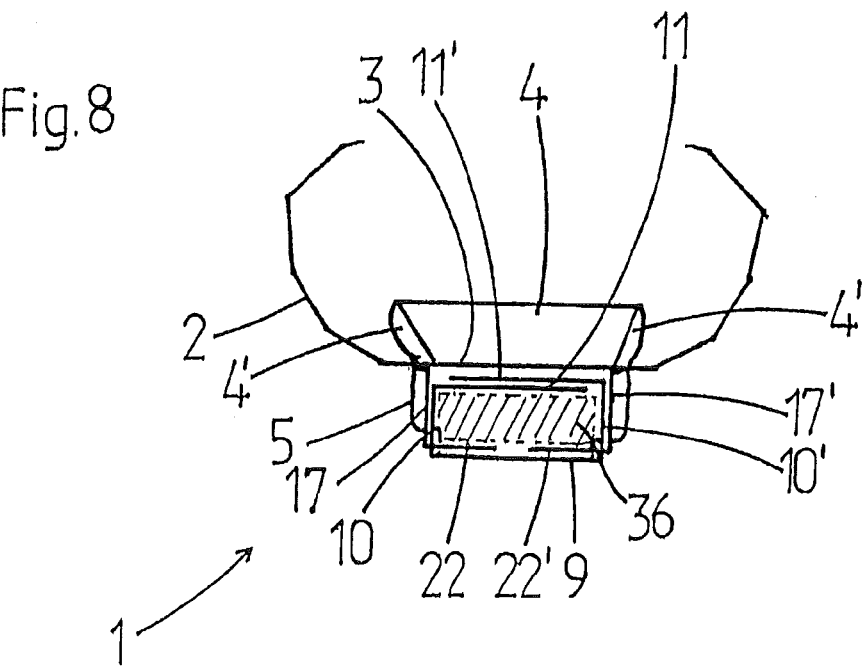
FIG. 8 shows a schematic rear view of the splint as per FIG. 7.

FIGS. 7 and 8 show schematically a side view and a rear view of another exemplary embodiment, which combines the components of the exemplary embodiment from FIG. 1 to 3 with a supporting member from FIG. 4 to 6. The splint 1 from FIG. 1 to 3 will not be presented again, reference being made to the discussion of FIG. 1 to 3.

The supporting member 6, which is rectangular in cross section, has a cavity that is suited to receiving a supporting member 36, 36', 36'' or 36'''. Separate adhesive bonding, riveting, strapping, etc., of the supporting member 36 to the contact surfaces 3, 4, 5 is not necessary in this place, since it is securely incorporated and fixed in the cavity of the supporting member 6, which is fixed by a strapping to the straps 17. Of course, it is also preferably possible to fasten the supporting member 36 to one of the inner sides of the supporting member 6 by means of an adhesive or another suitable fixation method, as already presented above. Thanks to the complementary shapes of the cavity in the supporting member 6 and the outside dimensions of the supporting member 36, however, a form-fit is created, so that the supporting member 36 is securely mounted in the supporting member 6 and performs its support function.

Figure 9:
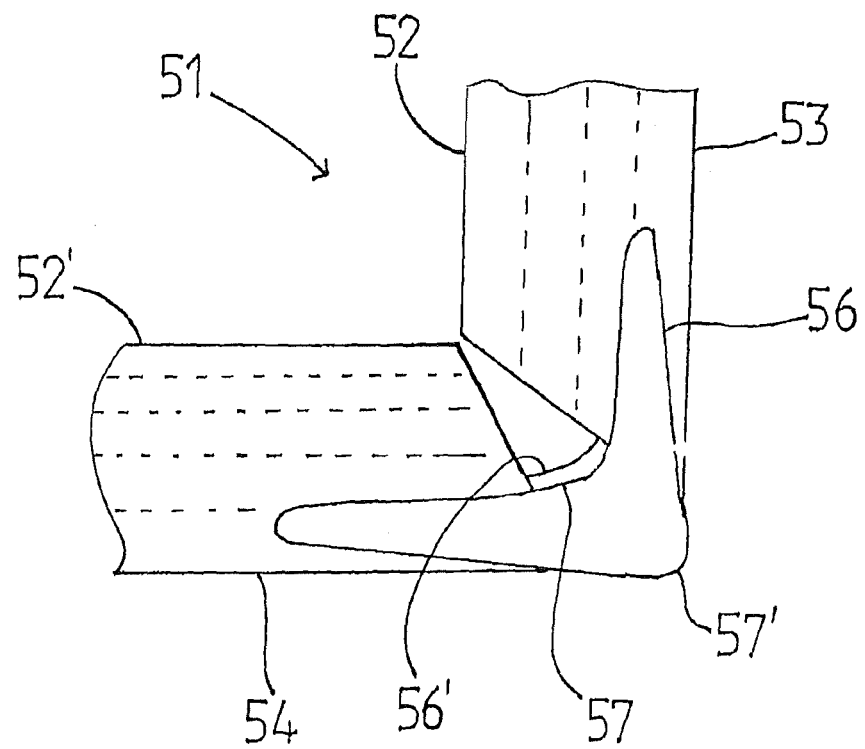
FIG. 9 shows a schematic side view of a splint according to the invention for an elbow joint or ankle joint.

FIG. 9 shows schematically a splint 51 according to the invention for an elbow joint or ankle joint, from the side. Flat bodies 52, 52' adjoining the joint and having a contact surface 53 for an upper arm and a contact surface 54 for a lower arm are shown partially. In the case of an ankle splint, the adjoining limbs would be the shin and the foot. The flat bodies 52, 52' can also be configured as uniform sleeves in which the joint to be immobilized is inserted.

At the site of the joint, two laterally arranged supporting members 56, 56' are shown, being joined at the side to the flat bodies 52, 52' in sheetlike manner, for example, by adhesive bonding or gluing. This dual design confers enhanced stability on the splint.

The angled outer contours of the flat body 56 are given the reference numbers 57, 57'. The supporting members 56, 56' are constructed from several interconnected layers of flat bodies, as already shown in FIG. 5 or 6, it being possible for the specific shape of the supporting member 56, 56' to be punched out. The individual layers of the supporting members 56, 56' lie in a direction perpendicular to the plane of the drawing, one on top of the other, in FIG. 9, such that the normals to the supporting members 56, 56' project from the plane of the drawing, as does the axis of the joint to be immobilized.

The supporting members 56, 56' have a slight projection beyond 90°, so that the upper arm or the elbow joint or the heel is protected against pressure. The projection is shown in FIG. 9 in the region of the start of the line leading to reference number 57'. The edge or the outer contour 57' here projects across at least one contact surface 53 or 54 or across both contact surfaces 53 and 54. In this way, sufficient room is provided for the elbow joint or the heel. Furthermore, better care of the supported joint is assured.

Figure 10:
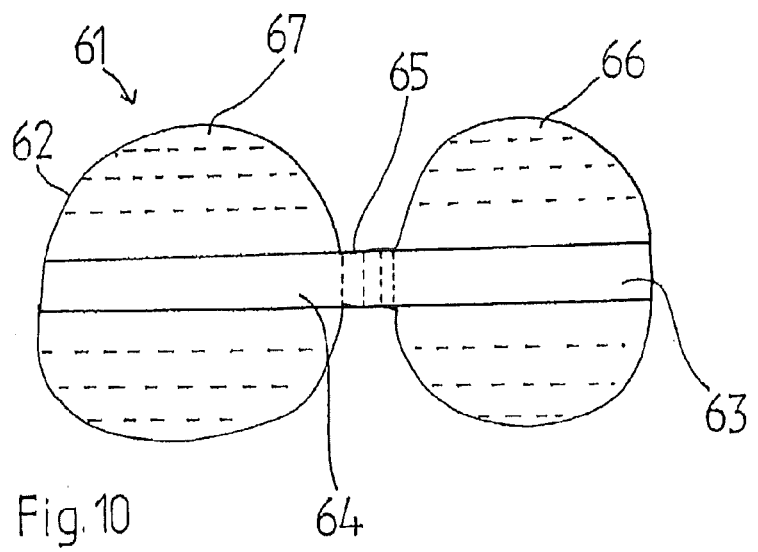
FIG. 10 shows a schematic top view of a flat body for a splint according to the invention for a knee joint.

FIG. 10 is a schematic top view of a flat body 62 for a splint 61 according to the invention for a knee joint. A preferred angle of bending for a knee joint to be immobilized is around 20°.

The flat body 62 has a contact surface 63 for a thigh and a contact surface 64 for a shin, which are adjoined at the side by surfaces 66, 67 for the thigh and shin, respectively. In the middle is arranged a cross-folded or perforated contact surface 65 for the hollow of a knee, which can be bent around the transverse fold lines or perforations in order to follow a knee bending by a specified angle.

Figure 11:
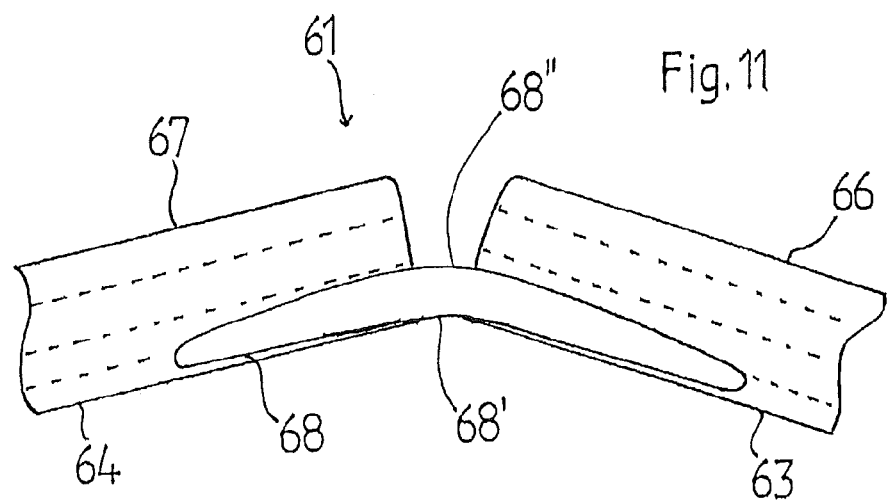
FIG. 11 shows a schematic side view of a splint according to the invention as per FIG. 10.

FIG. 11 shows a splint 61 from FIG. 10 schematically from the side. A supporting member 68, which can be configured as shown in FIG. 5, is joined at the side to the flat body 62, especially to the side surfaces 66, 67. The normal to the supporting member 68 is essentially parallel to the axis of the knee joint or has an angle of up to 45° or 60° to the axis of the knee joint. The angled outer contours of the supporting member 68 are given the reference numbers 68', 68".

Figure 12:
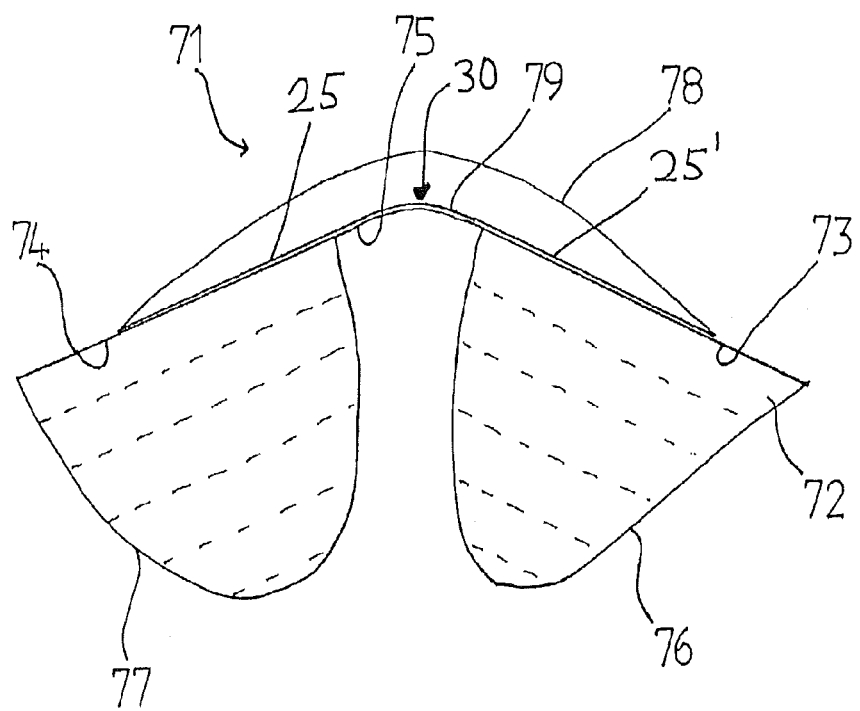
FIG. 12 shows a schematic side view of another splint according to the invention for a knee joint.

FIG. 12 shows schematically from the side an alternative splint 71 according to the invention for a knee joint. A flat body 72 with contact surfaces 73, 74, 75 for a thigh, a shin, and a knee cap is configured to be applied to the outside of a knee joint. Side surfaces 77, 78 are folded around the adjoining limbs. On the outside of the flat body 72, i.e., on the side facing away from the knee joint, there is placed a supporting member 78, which has a concave inner surface as the outer contour 79. By the concave inner surface, the supporting member 78 is joined to the outside of the flat body 72. The outer contour 79 has a rounded edge 30.

The imaginary extensions of the outer contour 79 make an angle which dictates the angle between the contact surfaces 73 and 74.

The supporting member 78 is constructed from flat bodies joined together in parallel, as shown in FIG. 5, 6, while the normal to the flat bodies is oriented parallel to the axis of the knee joint.

Alternatively, the supporting members 68 from FIG. 11 can also be used, in that they are adhesively bonded to each other roughly at the width of the hollow of a knee and inserted into the hollow of a knee. In particular, the supporting members 68 from FIG. 11 and the supporting members 78 from FIG. 12 can have the same shape and be used alternatively in the positions shown in FIG. 11 and FIG. 12. Preferably the convex side is adapted to the shape of the hollow of a knee and the concave side to the shape of the outside of a knee with a knee cap.

In the exemplary embodiments shown in FIGS. 4-8 and 12, instead of a centrally arranged supporting member one can also use a pair or a plurality of supporting members arranged and/or oriented essentially in parallel.

Figure 13:
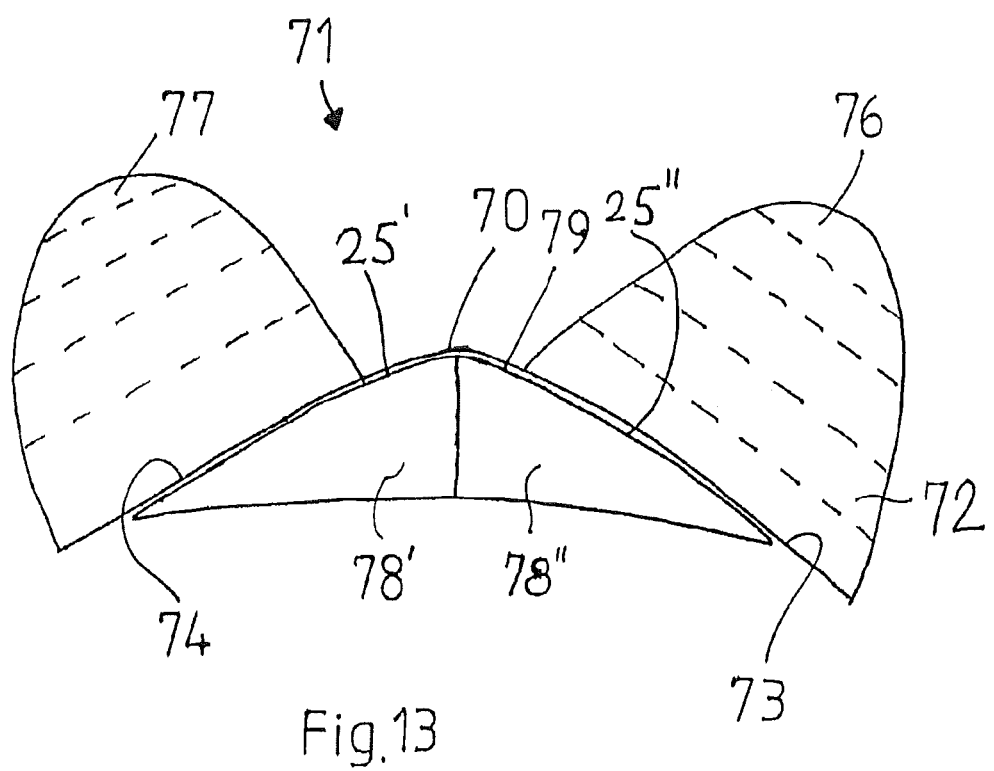
FIG. 13 shows a schematic side view of another splint according to the invention for a knee joint.

FIG. 13 shows a schematic side view of another splint 71 according to the invention for a knee joint. Here, the contact surface 73 for a thigh and the contact surface 74 for a shin are configured so that the hollow of a knee can bear against these surfaces. For this, the reference number 70 is also provided as contact surface for the hollow of a knee. By means of the side surfaces 76 and 77 for the thigh and the shin respectively, the latter can be secured accordingly. In order to specify a corresponding angle between the contact surfaces 73 and 74, two supporting members 78' and 78" are provided, being arranged adjacent to each other and joined to the flat body 72.

The two supporting members 78' and 78" can also be called shaped bodies and they have a three-dimensional shape, which can have roughly the depth of the contact surfaces 73 and 74. The mutually adjoining surfaces of the supporting members 78 and 78' can also be adhesively bonded to each other or joined by another connection, such as a hook-and-eye connection. The outer contours 79 of the supporting members 78' and 78" have shaped body surfaces 25' and 25", which are joined to the flat body 72. The supporting members 78' and 78" as well as the flat body 72 can be stored separate from each other and thus require little packing space. These can then be joined together when used.

Figure 14:
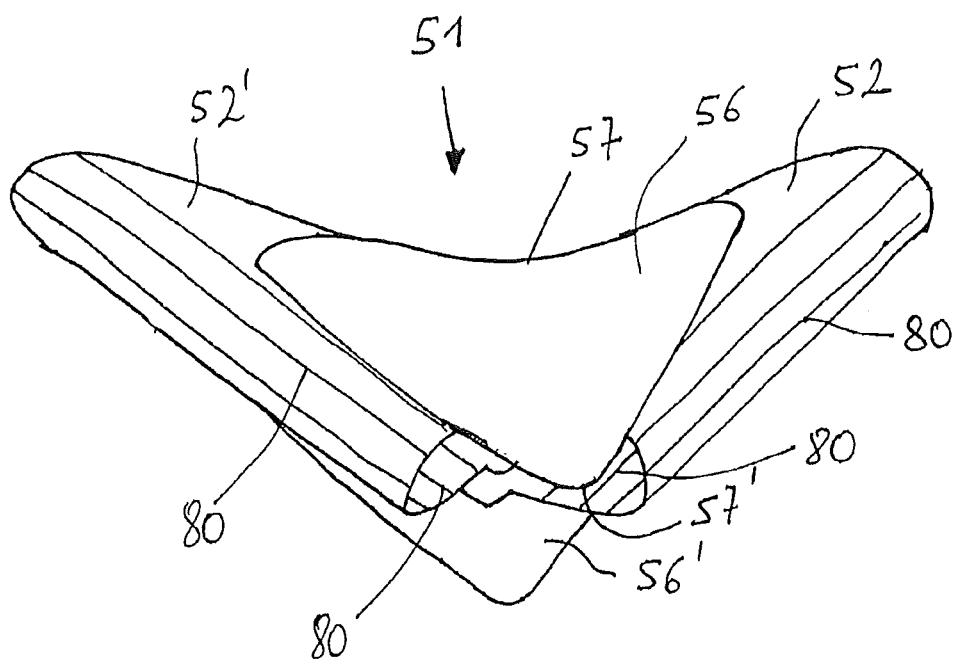
FIG. 14 shows a schematic three-dimensional representation of a splint according to the invention for an elbow joint or ankle joint in another configuration.
Figure 15:
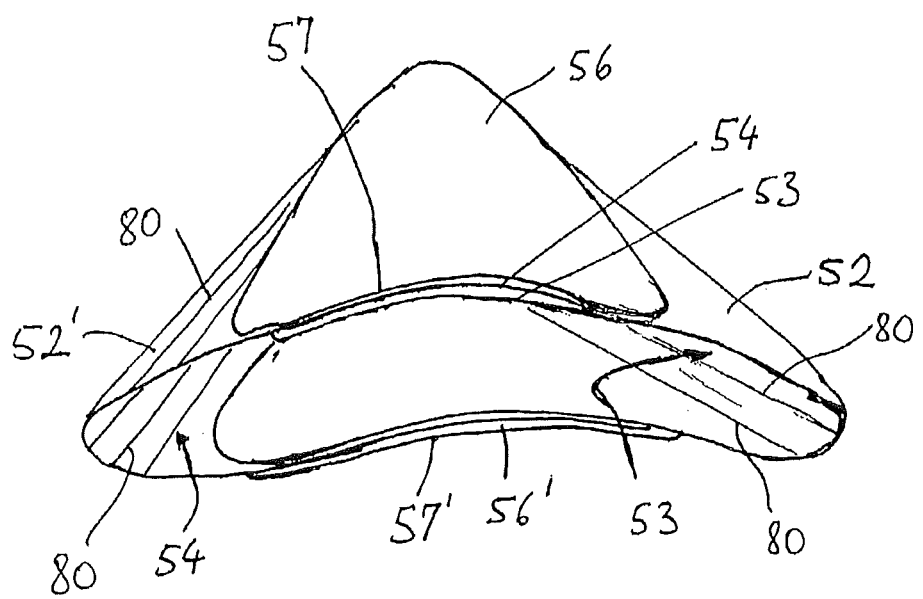
FIG. 15 shows the embodiment as per FIG. 14 in a schematic three-dimensional representation shown from a different direction.

FIG. 14 shows a schematic three-dimensional representation of a splint 51 according to the invention for an elbow joint or ankle joint in another configuration. Two flat bodies 52 and 52' are joined together. The flat body 52 has a contact surface for an upper arm. This is given the reference number 53 in FIG. 15. Furthermore, fold lines 80 are provided, enabling quick and easy adaptation to the corresponding roundness of the upper arm. Accordingly, the flat body 52' has a contact surface 54 for a forearm, which can be seen in FIG. 15. The connection of the two flat bodies 52 and 52' occurs by adhesive bonding or some other connection. Adhesive bonding, however, is preferred here. In this way, the flat bodies 52 and 52' are already joined immovably to each other. In addition, additional stabilization on each side is provided by a supporting member 56 and 56', which are also joined immovably to each other by the flat bodies 52 and 52'. In the embodiment of the invention according to FIGS. 14 and 15, the contact surface 54 for a forearm also serves at the same time as a supporting member, namely in the region where the supporting members 56 and 56' are each joined to the contact surface 54 for a forearm. This affords a double-wall structure and immovable joining-together according to the invention. This can be seen particularly well in FIG. 15, where the double-wall structure of the respective supporting member can be clearly seen. Overall, this gives a wall of threefold thickness in places with the flat body 52. This is correspondingly stable.

The flat bodies 52 and 52' can also be joined together accurately via the outer contours 57 and 57' of the respective supporting member 56 and 56', so that a predeterminable angle is produced between the imaginarily extended contact surfaces 53 and 54. Furthermore, the supporting member 56 or 56' projects slightly beyond this point or line of intersection, so that the elbow joint or the heel can be securely mounted accordingly. The outer contours 57 and 57' lie in places flush above the outer contours of the flat bodies 52 and 52'. In this way, an accurate connection of the supporting members to the flat bodies is possible, so that a predeterminable angle can be produced between the contact surfaces.

All mentioned features, including those only found in the drawings, as well as individual features that are disclosed in combination with other features, are deemed to be essential to the invention alone and in combination. Embodiments according to the invention can be fulfilled by individual features or a combination of several features.

LIST OF REFERENCE SYMBOLS 1 splint
2 flat body
3 contact surface for a forearm
4 contact surface for the palm of a hand
4' contact surface for a thumb
5 contact surface for fingers 6 supporting member
7 outer contour
8, 8' angle structure
9 bottom
10, 10' side surface
11, 11' top
12, 12' bottom fold line
13, 13' slit
14, 15, 16 transverse fold
17, 17' strap
18, 18' strap fold line in the contact surface
19, 19' strap fold line in the strap
20, 20' lengthwise fold line
21 recess for strap
22, 22' strap insert piece
25, 25', 25" surface of shaped body
30, 30', 30"
30''', 30'''' edge
31 splint
32 flat body
33 contact surface for a forearm
34 contact surface for the palm of a hand
34' contact surface for thumb
35 contact surface for finger
36-36''' supporting member
37 outer contour
38, 38' angle structure
39-39" flat body
40 rivet
41 strapping
42 round head clamps
51 splint
52, 52' flat body
53 contact surface for an upper arm
54 contact surface for a forearm
56, 56' supporting member
57, 57' outer contour
61 splint
62 flat body
63 contact surface for a thigh
64 contact surface for a shin
65 contact surface for the hollow of a knee
66 side surface for thigh
67 side surface for shin
68 supporting member
68',68" outer contour
70 contact surface for hollow of knee
71 splint
72 flat body
73 contact surface for a thigh
74 contact surface for a shin
75 contact surface for a knee cap
76 side surface for thigh
77 side surface for shin
78, 78', 78" supporting member
79 outer contour
80 fold line

What is claimed is:

1. A knee immobilization splint, comprising:
    (a) a first panel and a second panel, each panel having a contact surface for being attached to respective upper and lower leg portions adjoining a knee to be immobilized; and
    (b) a support member connecting the first panel and the second panel and including a rigid angled structure for bracing the upper and lower leg portions at a predetermined desired angle relative to each other for immobilizing the knee and the respective upper and lower leg portions adjoining the knee, the support member including a plurality of material layers having edges and lateral faces in which the lateral faces are stacked together to form the support member and the support member is positioned in the knee immobilization splint such that one edge of each material layer is configured to be positioned directly adjacent to a dorsal portion of the knee and the opposing edge of each material layer is positioned away from the dorsal portion of the knee, wherein:
    each material layer of the support member is fixed relative to the other material layers of the support member; and
    the first and second panels are immovably joined by the support member such that movement of the first and second panels is prevented in a lengthwise direction of the splint as well as perpendicular direction relative to the contact surface of each panel when the knee immobilization splint is in use.

2. The splint as claimed in claim 1, wherein the first panel, the second panel, and the support member each comprise a single-piece flat body which is adapted for folding into a three-dimensional form.

3. The splint as claimed in claim 2, wherein the first panel, the second panel, and the support member each comprise cardboard.

4. The splint as claimed in claim 3, wherein the connection between the first panel and the support member, the second panel and the support member, and between each layer of the plurality of adjacent material layers comprises an adhesive, clamping, strapping, or a hook-and-eye connection.

5. The splint according to claim 3 wherein the support member has a cross-folded surface located between the attachment of the first and second panel, the cross-folded surface having a plurality of transverse fold lines or perforations configured for following a knee bending by the desired angle.

6. The splint according to claim 3 wherein the support member has a plurality of transverse fold lines or perforations positioned between the attachment of the first and second panel and extending an entire width of the support member, which is configured to be positioned directly adjacent to a dorsal portion of the knee.

7. The splint as claimed in claim 1, wherein the support member is formed from a sheet material and the plurality of adjacent material layers are folded from the sheet material.

8. A knee immobilization splint comprising:
    a. a support member configured for placement adjacent a dorsal portion of the knee, and to extend from a thigh portion of a leg to a shin portion of the leg, the support member comprising a rigid angled structure for bracing and immobilizing the knee, thigh portion of the leg, and the shin portion of the leg at a predetermined desired angle, and including a plurality of material layers having edges and lateral faces in which the lateral faces are stacked together to form the support member and the support member is positioned in the knee immobilization splint such that one edge of each material layer is configured to be positioned directly adjacent to a dorsal portion of the knee and the opposing edge of each material layer is positioned away from the dorsal portion of the knee;
    b. a first panel fixed to an inner side of the support member, adapted for folding and securing around the thigh portion of the leg;

c. a second panel fixed to the inner side of the support member, adapted for folding and securing around the shin portion of the leg; and d. wherein, when the first panel is configured to be folded and secured around the thigh portion of the leg and the second panel is configured to be folded and secured around the shin portion of the leg, the splint is configured to immobilize the knee, the thigh portion of the leg, and the shin portion the leg at the predetermined desired angle such that movement of the first and second panels is prevented in a lengthwise direction of the knee immobilization splint as well as a perpendicular direction relative to a contact surface of each panel when the knee immobilization splint is in use.

9. The splint according to claim 8 wherein the support member, the first panel, and the second panel comprise cardboard.

10. The splint according to claim 9 wherein the support member has a plurality of transverse fold lines or perforations positioned between the attachment of the first and second panel and extending an entire width of the support member, which is configured to be positioned directly adjacent to a dorsal portion of the knee.

11. The splint according to claim 8, wherein the support member is a sheet material adapted for folding into a three-dimensional form according to the desired angle and for configuring first and second panels.

12. The splint according to claim 8 wherein the support member has a cross-folded surface, located between the attachment of the first and second panel, and having a plurality of transverse fold lines or perforations configured for following a knee bending by the desired angle.

13. The splint according to claim 8 wherein the plurality of joined flat layers are joined via an adhesive, clamping, strapping, or a hook-and-eye connection.

14. The splint according to claim 8 wherein ends of the first and second panels are joined around the respective thigh and shin portions of the leg via an adhesive, clamping, strapping, or a hook-and-eye connection.

15. A knee immobilization splint comprising:

a. a support member configured for placement parallel to an upper surface of the knee above the knee cap, extending from the thigh portion of the leg to the shin portion of the leg, the support member comprising a concave inner surface, a rounded outer surface, a rigid angled structure configured for bracing and immobilizing the knee, the thigh portion of the leg, and the shin portion of the leg at a predetermined desired angle, and including a plurality of material layers having edges and lateral faces in which the lateral faces are stacked together to form the support member in which the support member is positioned in the knee immobilization splint such that one edge of each material layer is configured to be positioned directly adjacent to a dorsal portion of the knee and the opposing edge of each material layer is positioned away from the dorsal portion of the knee;

b. a first panel fixed to an underside of the support member, and adapted for folding and securing around the thigh portion of the leg;

c. a second panel fixed to and underside the support member, and adapted for folding and securing around the shin portion of the leg; and d. wherein, when the first panel is configured to be folded and secured around the thigh portion of the leg and the second panel is configured to be folded and secured around the shin portion of the leg, the knee, thigh portion of the leg, and the shin portion of the leg are configured to be fixed and immobilized at the predetermined desired angle by the support member such that movement of the first and second panels is prevented in a lengthwise direction of the knee immobilization splint as well as a perpendicular direction relative to a contact surface of each panel when the knee immobilization splint is in use.

16. The splint according to claim 15, wherein the support member is a sheet material adapted for folding into a three-dimensional form according to the desired angle and for configuring first and second panels.

17. The splint according to claim 16 wherein the support member has a cross-folded surface, located between the attachment of the first and second panel, and having a plurality of transverse fold lines or perforations configured for following a knee bending by the desired angle.

18. The splint according to claim 15 wherein the support member, the first panel, and the second panel comprise cardboard.

19. The splint according to claim 15 wherein the plurality of joined flat layers are joined via an adhesive, clamping, strapping, or a hook-and-eye connection.

20. The splint according to claim 15 wherein ends of first and second panels are joined around the respective thigh and shin via an adhesive, clamping, strapping, or a hook-and-eye connection.

* * * * *